United States Patent [19]
Wholey et al.

[11] Patent Number: 5,254,127
[45] Date of Patent: Oct. 19, 1993

[54] METHOD AND APPARATUS FOR CONNECTING AND CLOSING SEVERED BLOOD VESSELS

[75] Inventors: Mark H. Wholey, Oakmont; William E. Novogradac, deceased, late of Pittsburgh, both of Pa., by Barbara J. Novogradac, Executrix

[73] Assignee: Shadyside Hospital, Pittsburgh, Pa.

[21] Appl. No.: 18,812

[22] Filed: Feb. 18, 1993

Related U.S. Application Data

[62] Division of Ser. No. 843,384, Feb. 28, 1992.

[51] Int. Cl.$^5$ ............................................. A61B 17/00
[52] U.S. Cl. ................................. 606/153; 606/155; 285/397
[58] Field of Search ................. 606/152-157, 606/213, 215, 216

[56] References Cited

U.S. PATENT DOCUMENTS

| | | | |
|---|---|---|---|
| 3,221,746 | 12/1965 | Noble | 606/155 |
| 3,266,113 | 8/1966 | Flanagan, Jr. | 24/204 |
| 3,981,051 | 9/1976 | Brumlik | 24/204 |
| 4,169,303 | 10/1979 | Lemelson | 24/204 |
| 4,214,587 | 7/1980 | Sakura | 606/155 |
| 4,593,693 | 6/1986 | Schenck | 606/155 |
| 4,665,917 | 5/1987 | Clanton et al. | 606/153 |
| 4,917,087 | 4/1990 | Walsh et al. | 606/155 |
| 4,920,235 | 4/1990 | Yamaguchi | 24/450 |
| 4,997,439 | 3/1991 | Chen | 606/213 |
| 5,047,047 | 9/1991 | Yuon | 606/216 |
| 5,123,908 | 6/1992 | Chen | 606/153 |
| 5,207,695 | 5/1993 | Trout, III | 606/153 |

OTHER PUBLICATIONS

H. Han et al., "A mechanical surface adhesive using micromachined silicon structures", *J. Micromech. Microeng.* 1 (1991), pp. 30-33.

Hongtao Han et al., "Mating and Piercing Micromechanical Structures for Surface Bonding Applications", a paper presented at the Microelectrical Mechanical Systems Workshop, Jan. 1992, in Nara, Japan.

*Primary Examiner*—Stephen C. Pellegrino
*Assistant Examiner*—Gary Jackson
*Attorney, Agent, or Firm*—Buchanan Ingersoll

[57] ABSTRACT

A device for closing or connecting blood vessels has a plurality of micro miniature barb which pierce the wall of the blood vessel and anchor the device in place. In one embodiment the fastener is comprised of a male member and a female member which are fastened to blood vessel segments with the micro miniature barbs. The male and female members are joined together by inserting the male member into the female member to form a permanent coupling. The device can also be used for opening a blood vessel which has been narrowed by disease or trauma.

6 Claims, 4 Drawing Sheets

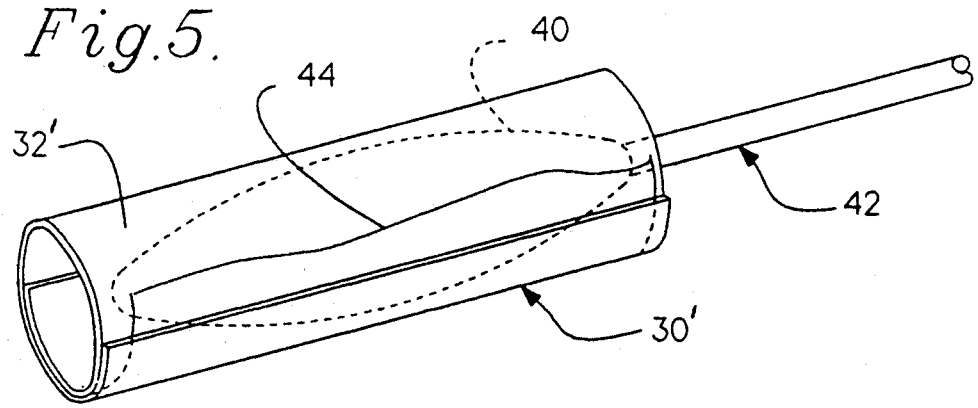
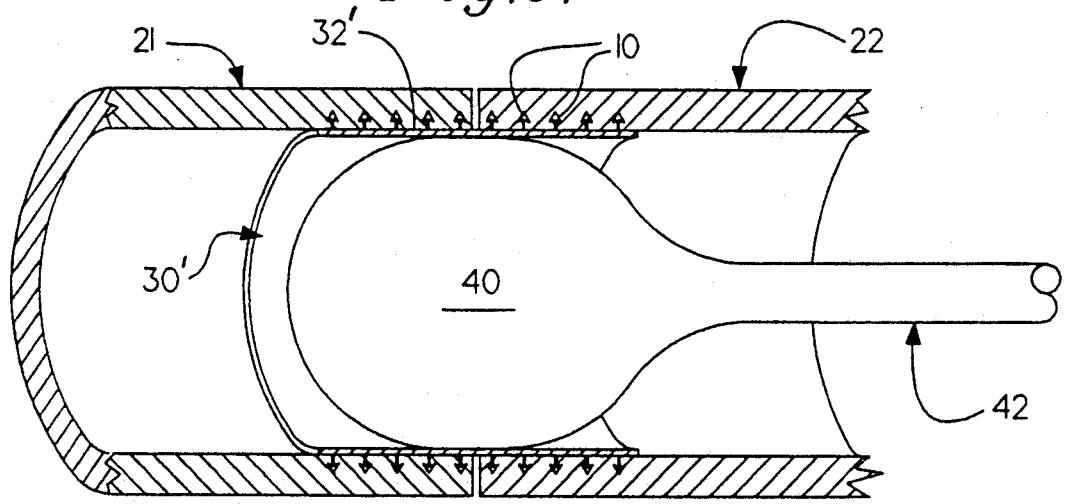
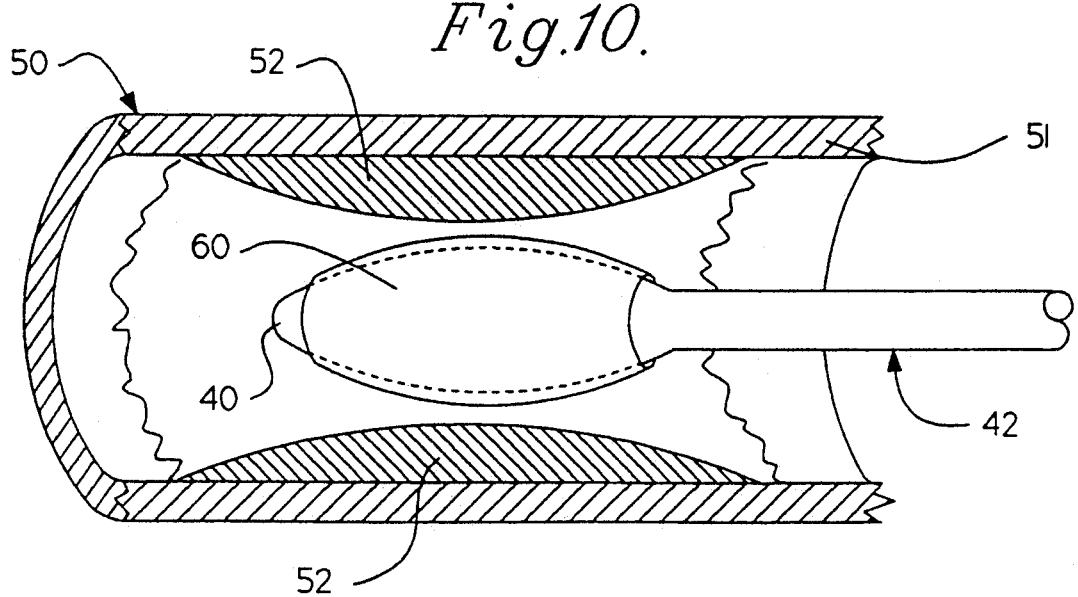

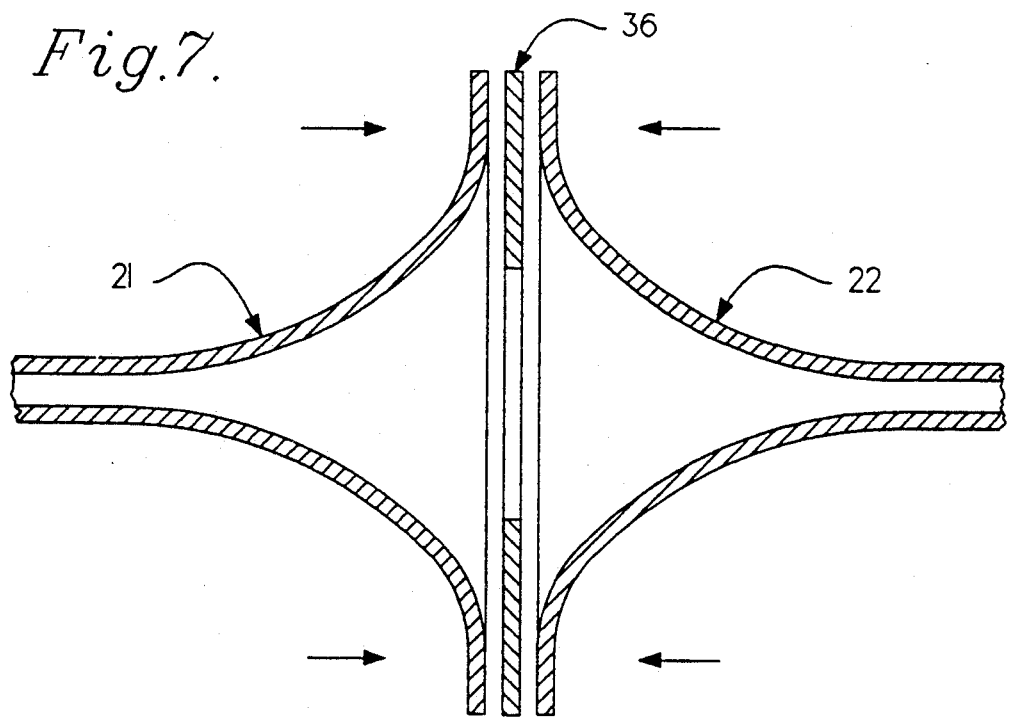
Fig.7.
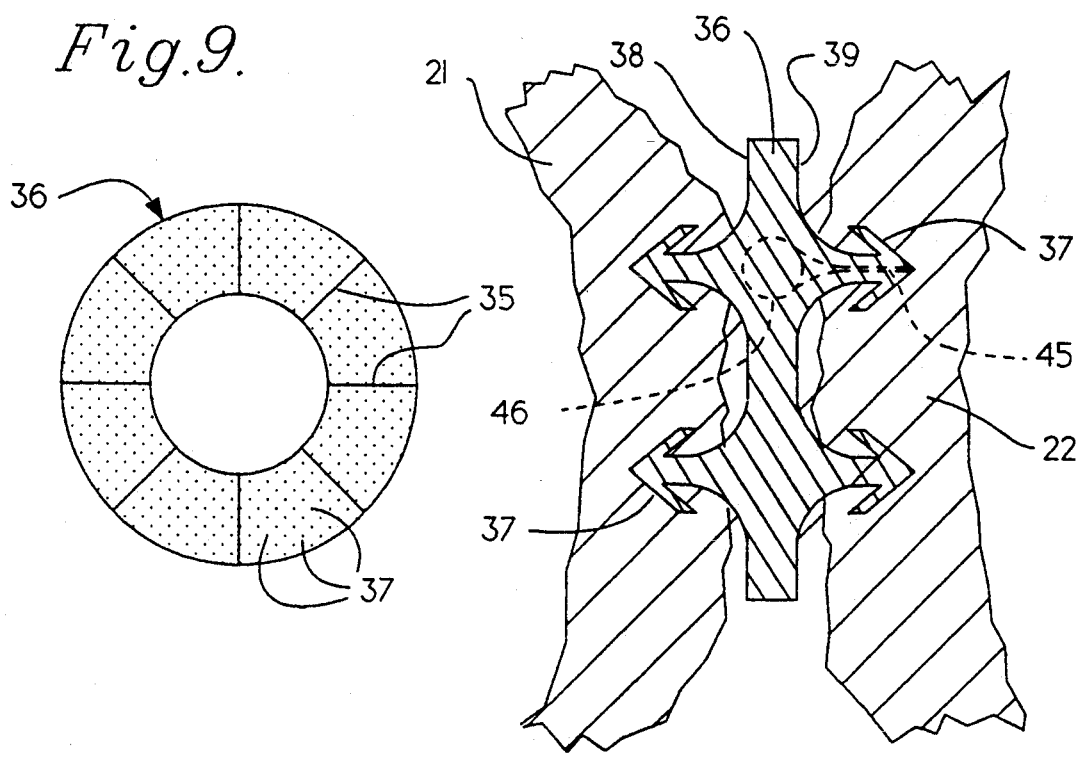
Fig.9.
Fig.8.

METHOD AND APPARATUS FOR CONNECTING AND CLOSING SEVERED BLOOD VESSELS

This application is a division of application Ser. No. 843,384, filed Feb. 28, 1992.

FIELD OF INVENTION

The invention relates to a method and apparatus for connecting or closing severed blood vessels which can be used as an alternative to suturing.

BACKGROUND OF INVENTION

Many surgical procedures involve partially or totally severed blood vessels which must be connected. The conventional method of reconnecting such vessels and closing incisions is by sewing them together with a suitable suture material. Although this procedure has been medically successful, it can involve considerable time during an operation. Thus, there is a need for a method and apparatus for quickly connecting or closing severed blood vessels.

Any device which can be used to quickly connect blood vessels together must be compatible with the human or animal body in which it is used. Since most blood vessels are flexible, it is desirable that any such device also be flexible.

We have developed a fastener for use in connecting blood vessels together. In one embodiment the fastener is comprised of a male member and female member which are fitted together with a one-way fastener. After the male member has engaged the female member the fastener cannot be disengaged without destroying the coupling. A portion of the exterior of the male member has a plurality of very small projections which are sized to engage a receiving surface on the interior of the female member. The receiving surface is constructed to receive the projections from the male member and make a permanent coupling therebetween. Both the male member and female member have a plurality of micro miniature barbs on at least a portion of their outer surfaces. Those barbs are positioned to penetrate the walls of the blood vessel and then hold the coupling in place against the blood vessel wall. The coupling may be inserted into the blood vessel by any convenient means. If the blood vessel has been severed or substantially cut open, the fastener's segments could be positioned through the opening created when the blood vessel was cut.

The second preferred embodiment is comprised of a flexible body having one surface from which a plurality of micro miniature barbs extend. The body is sized so as to extend around at least a portion of the inner surface or outer surface of the blood vessel. Preferably the body is a compressible hollow cylinder or a flat sheet which can be rolled to a dimension smaller than the blood vessel, inserted in the blood vessel and then expanded to engage the inside wall of the blood vessel. A preferred way of inserting this embodiment is to wrap the flexible body around a balloon catheter and extend the catheter into the vessel to the location where fastening or closure is required. Then the balloon is inflated to unroll the fastener and press it tightly against the inside wall of the blood vessel.

Other objects and advantages of our micro miniature blood vessel closure and fastener and method of inserting same will become apparent from a description of the present preferred embodiments shown in the drawings.

BRIEF DESCRIPTION OF THE DRAWINGS

FIG. 5 is a perspective view partially in section of the present preferred embodiment of our device in a rolled position.

FIG. 6 is a perspective view partially in section of the device of FIG. 5 in an unrolled expanded position.

FIG. 7 is a cross-sectional view showing another preferred embodiment of our device.

FIG. 8 is an enlarged view of a portion of the embodiment of FIG. 7.

FIG. 9 is a plan view of the embodiment shown in FIGS. 7 and 8.

FIG. 10 is a cross-sectional view showing our device used in a blood vessel which has been narrowed by disease or trauma.

DESCRIPTION OF THE PREFERRED EMBODIMENTS

Figure 1:
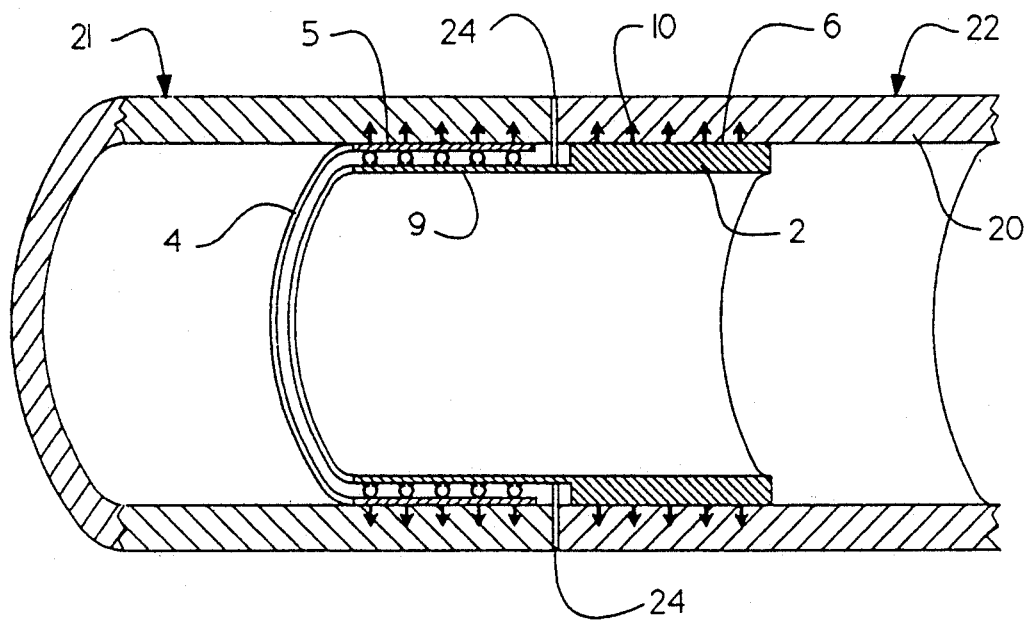
FIG. 1 is a cross sectional view of a portion of a blood vessel containing a first present preferred embodiment of our device being used to attach blood vessel segments.
Figure 2:
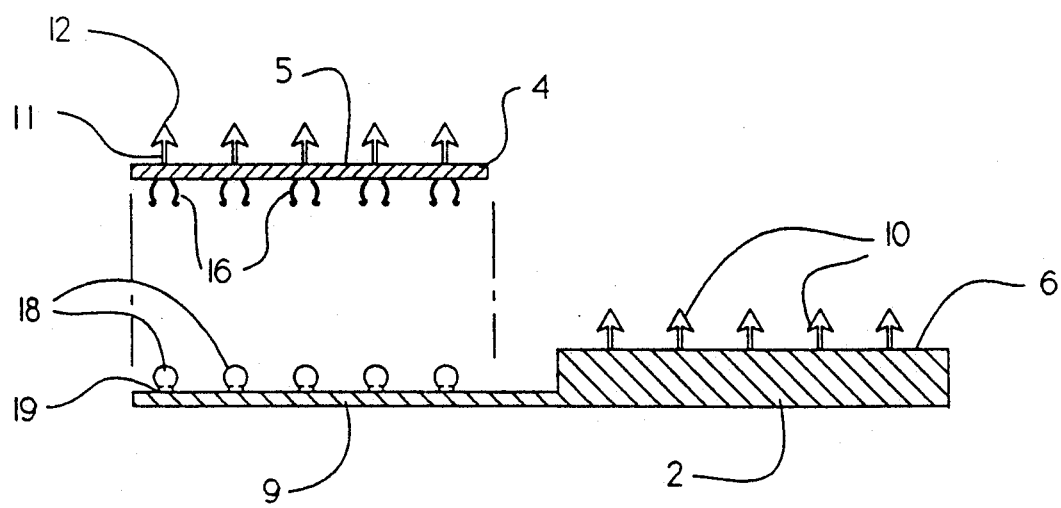
FIG. 2 is an exploded view of a segment of the device shown in FIG. 1.

Referring to FIGS. 1 and 2 a first preferred embodiment used as a fastener is comprised of a male member 2 and female member 4 which are connected to form of stent. Both the male member and female member are generally cylindrical. They should be made of a flexible material. On the outer surface 5 of the female member and a first portion of the outer surface 6 of the male member we provide a plurality of micro barbs 10. The micro barbs are sized to extend into the wall 20 of blood vessel segments 21 and 22. The segments may have been completely detached or only partly separated from one another by an incision which created gap 24. The micro barbs are generally comprised of a stem 11 and at least one barb 12 which may be of a triangular configurations as shown in FIGS. 1 and 2. Alternatively, one could use tiny fish hook structures or other shapes which can be firmly embedded into the blood vessel wall. On the inner surface of the female member 4 and on a second portion 9 of the outer surface of the male member 2 we provide mating fastening members which engage to form a permanent connection between the male member and the female member. In the embodiment of FIG. 1 fastening means 16 are generally hemispherical in shape and adapted to receive pods 18 which extend from stems 19 attached to portion 9 of the male member 2. The male member 2 and female member 4 should be made of a flexible biocompatible material. One suitable material is silicon. Some plastics of the type used for other types of implantable structures may also be appropriate.

In FIGS. 1 and 2 we have shown a fastening means using a pod on a stem which fits into a hemisphere to form a locked connection. Various other configurations are known in the art which can also be used. For example, one could provide a doughnut shape into which the pods extend rather than the hemisphere 16. Similarly pods 18 could be triangular and inserted into a similarly contoured receiving member.

Figure 3:
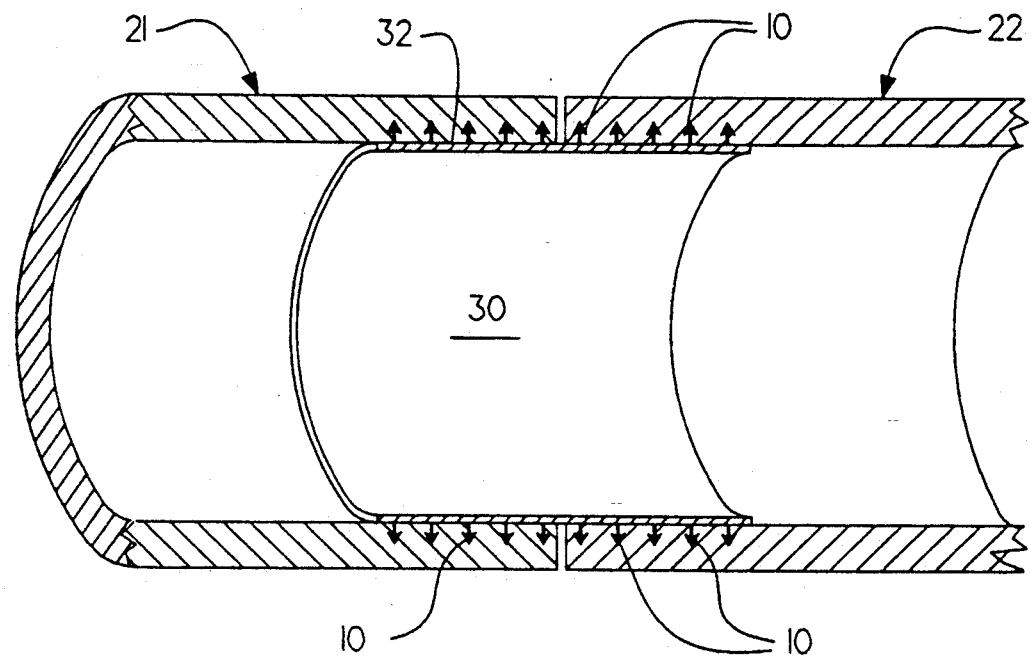
FIG. 3 is a side view partially in section of a second preferred embodiment of our device placed within a blood vessel.
Figure 4:
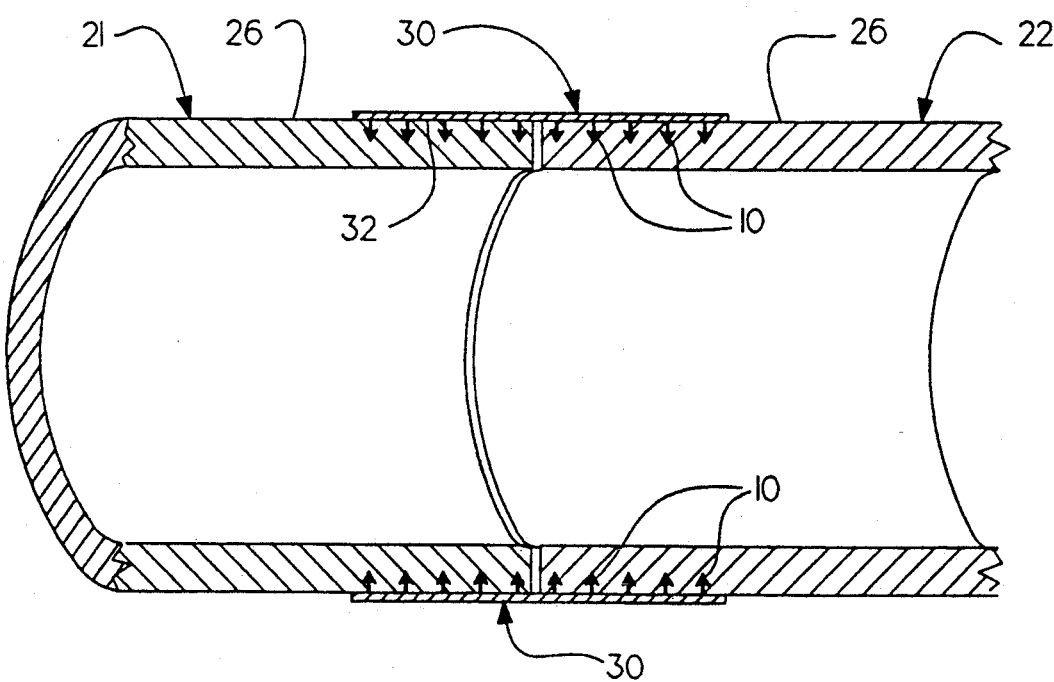
FIG. 4 is a side view partially in section of the device of FIG. 3 placed on the exterior of a blood vessel.

In FIGS. 3 and 4 we show a second preferred embodiment of our device 30 which is comprised of a flexible material having a plurality of barbs 10 extending from one surface 32 of the closure 30. The closure could be positioned as a stent within the blood vessel as shown in FIG. 3 so that the barb surface engages and anchors the closure to the inner wall of the blood vessel. Alternatively, this closure can be wrapped around the outside of the blood vessel as shown in FIG. 4 so that the barbs penetrate and embed within the outer surface 26 of blood vessel segments 21 and 22.

We prefer to make the embodiment of FIGS. 3 and 4, and both the male member and female member of the embodiment shown in FIGS. 1 and 2, of a flexible sheet which can be rolled to a diameter smaller than the inside diameter of the blood vessel. The rolled structure is placed at the juncture point of the vessel to be fastened and then expanded to engage the interior wall of the blood vessel.

In FIG. 5 we show the female member which has been rolled to a smaller diameter and placed upon balloon portion 40 a balloon catheter 42. It should be noticed that the inner surface of the female member 2 is separated from an overlapping portion of the outer surface 6 of the female member by a flap 44 extending from a balloon catheter 42. After the female member is located in the proper position the balloon portion 40 is inflated thereby unrolling the female member 2. As shown in FIG. 6 after unrolling the device, micro barbs 10 penetrate the blood vessel wall and anchor the female member in place. The male member 2 is inserted in a similar fashion. However, since the interior surface of the male member is smooth it is not necessary to provide a flap to separate adjacent surfaces of the male member when it is in a rolled position.

Referring to FIGS. 7, 8 and 9 we provide another embodiment comprised of a ring shaped body 36 having a plurality of micro miniature barbs 37 on opposite faces 38 and 39 the ends of the blood vessel segments are splayed. Then the inside wall portion of the vessels are pressed against a barbed face. The barbs penetrate the vessels joining them until tissue regrowth takes place. Placing the connector on the inside of the vessel avoids the difficulties associated with ring-and-pin type connectors. In this embodiment the splayed ends provide a larger passageway for blood flow than in the embodiments of FIGS. 1 and 3. By holding the vessel open, regrowth of the tissue over the stent would be facilitated while the maximum blood flow rate is maintained. To provide flexibility, we may provide score lines 35 on faces 38 and 39. The ring could also be made of a 10 radially compressible material. Then the ring 36 could be placed in position and caused to expand thru use of a balloon catheter as in FIG. 6 or as a result of the memory of the material.

Our device can be used to open vessels that have been narrowed from disease or trauma. In FIG. 10 we show a partially occluded blood vessel 50 which has been constricted by deposits 52. Our device 60, is inserted with a balloon catheter 42. The balloon portion 40 of the catheter 42 is expanded (see FIG. 6) to attach the device to the wall 51 of the vessel 50 at the disease site. Then the balloon portion 42 is deflated and the catheter is removed. Our device remains in place to maintain lumen thru the diseased site.

In all of the embodiments passageways can be provided in the barbs. By fabricating each of the barbs with a passageway 45 and reservoir 46, shown in chain line in FIG. 8, the barbed face of the closure could act as a surface of microscopic hypodermic needles. Connection of the passageways to a larger reservoir (not shown) would provide a method of local drug delivery to a specific organ, rather than the bloodstream.

Silicon arrays of these piercing microstructures have been fabricated and having 4 μm high barbs and tested for gross adhesive capability. One-sided arrays, approximately 1 cm² square, were pressed into sections of a human vena cava obtained from a cadaver. The samples successfully bonded to the tissue, but the tensile strength is, as yet, below that required for clinical application. Electron micrographs of delaminated tissue showed four distinct regions which were characterized by several features. Holes occurred where the barbs penetrated and retracted from the tissue. Some barbs broke where penetration and bonding took place, but the silicon pedestal supporting the pointed cap failed. Intact pieces of silicon bonded to the issue. The silicon substrate itself fractured, probably during insertion. The epithelial lining separated from the vessel wall, with the mcirostructure arrays remaining bonded to the lining.

From this test it became clear that the barbs need to have a scale comparable to the thickness of the vessel wall for satisfactory bonding. We prefer to have structures on the order of 50 to 100 μm high, or greater.

Although our structures were made using a photolithographic process other techniques could be used. For example, micromachining, crystal growing methods, vapor deposition, particle beam manufacturing and other techniques for creating microstructures are possibilities.

Although we have described and shown certain present preferred embodiments of our closure and fastener and method of inserting same, it should be distinctly understood that our invention is not limited thereto but may be variously embodied within the scope of the following claims.

We claim:

1. A micro fastener for connecting blood vessels and portions of blood vessels comprising:
    a. a female member adapted to conform to an inner wall of the blood vessel, the female member having an outer surface and an inner surface;
    b. a male member adapted to conform to an inner wall of the blood vessel, the male member having a first outer surface portion sized and positioned to engage the inner surface of the female member and also having a second outer surface portion;
    c. a plurality of barbs sized to pierce and anchor in a blood vessel wall, the barbs attached to and extending from the outer surface of the female member and extending from a second outer surface portion of the male member;
    d. a first fastening means attached to the inner surface of the female member; and
    e. a second fastening means attached to the first outer surface portion of the male member
the first and second fastening means sized and configured to engage one another to lock the male member to the female member.

2. The micro fastener of claim 1 wherein the first fastening means is comprised of a plurality of hemispherical projections and the second fastening means are comprised of a plurality of projections having a stem and pod each pod being sized to fit within a hemispherical projection.

3. The micro fastener of claim 1 wherein the male member and the female member are comprised of a flexible material so that said members can be rolled into a diameter smaller than a blood vessel diameter, inserted into the blood vessel and unrolled to engage the inner wall of the blood vessel.

4. The micro fastener of claim 1 wherein the male member and the female member are able to be compressed to a diameter smaller than a blood vessel diameter, inserted into the blood vessel in a compressed condition and there allowed to expand and anchor the male member and the female member to the inner wall of the blood vessel.

5. The micro fastener of claim 1 wherein the barbs extend 50 μm to 100 μm from the outer surface.

6. The micro fastener of claim 1 wherein the barbs contain a passageway through which a fluid may flow from a reservoir.

* * * * *